(12) United States Patent
Rajasekharan

(10) Patent No.: US 10,539,529 B2
(45) Date of Patent: Jan. 21, 2020

(54) DETERMINATION OF ANALYTES USING ELECTROCHEMICALLY ACTIVE INDICATOR SPECIES AS REACTANTS

(71) Applicant: HACH COMPANY, Loveland, CO (US)

(72) Inventor: Vishnu V Rajasekharan, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 171 days.

(21) Appl. No.: 15/690,587

(22) Filed: Aug. 30, 2017

(65) Prior Publication Data

US 2018/0059057 A1     Mar. 1, 2018

Related U.S. Application Data

(60) Provisional application No. 62/381,317, filed on Aug. 30, 2016.

(51) Int. Cl.
   *G01N 27/49*        (2006.01)
(52) U.S. Cl.
   CPC ................... *G01N 27/49* (2013.01)
(58) Field of Classification Search
   None
   See application file for complete search history.

(56) References Cited

U.S. PATENT DOCUMENTS

| | | |
|---|---|---|
| 2008/0047846 A1 | 2/2008 | Salzer |
| 2015/0108009 A1* | 4/2015 | Rajasekharan .... G01N 33/1806 205/785.5 |
| 2015/0285779 A1 | 10/2015 | West et al. |

FOREIGN PATENT DOCUMENTS

JP    H09127053    5/1997

OTHER PUBLICATIONS

International Search Report and The Written Opinion of the International Searching Authority, dated Jan. 5, 2018, 13 pages.

* cited by examiner

*Primary Examiner* — Eli S Mekhlin
(74) *Attorney, Agent, or Firm* — Ference & Associates LLC

(57) ABSTRACT

A method for determination of an unknown analyte using quantitative electrochemical generation of a detectable species, which provides specified quantities of the species, is described. As an example, free chlorine concentration measurements may be performed using N,N-Diethyl-p-phenylenediamine (DPD), or N,N-bis(2,4-di-sulfobenzyl)toluidinetetrasodium salt (SBT), for obtaining an in-situ calibration curve, whereby matrix effects are eliminated.

6 Claims, 4 Drawing Sheets

DETERMINATION OF ANALYTES USING ELECTROCHEMICALLY ACTIVE INDICATOR SPECIES AS REACTANTS

BACKGROUND OF THE INVENTION

Many analyte determination procedures require calibration protocols, which add to the complexity of the analysis and increase cost and analysis time affecting the performance of the sensor. Matrix effects associated with standard solutions for analyses induce errors, especially when analyte concentrations are either very high or very low. For example, the lower range of analyte concentrations includes parts per billion, while the higher range might include greater than 75-80% of the analyte in the sample matrix. In particular, measurements of disinfectant concentrations, such as for chlorine, or nutrient concentrations, such as for phosphates, or disinfection by-products such as nitrosamines, require calibration protocols.

BRIEF SUMMARY OF THE INVENTION

In general, the present disclosure is directed to a method of determining the concentration of an analyte using a combination of chemical and electrochemical redox reactions, without the need for a calibration step.

In accordance with the purposes of the present invention, as embodied and broadly described herein, the method for determination of the concentration of an analyte in a solution, includes providing a sample of the solution including the analyte; adding to the solution a molar excess of an electrochemically and chemically oxidizable or reducible indicator species which forms an oxidized or reduced species when contacted by the analyte; allowing the indicator species to be chemically oxidized or reduced by the analyte to provide an oxidized or reduced indicator species; measuring a signal corresponding to the oxidized or reduced indicator species after chemical oxidization or reduction thereof by the analyte; electrochemically oxidizing or reducing the indicator species at a chosen voltage for a selected time period, whereby a first electrochemical oxidation or reduction charge is passed; recording the first electrochemical oxidation or reduction charge; measuring a signal corresponding to the oxidized or reduction indicator species after the step of electrochemically oxidizing or reducing the indicator species; repeating the step of electrochemically oxidizing or reducing the indicator species at least a second time, whereby at least one second oxidation or reduction charge is passed; recording the at least one second electrochemical oxidation or reduction charge; and measuring a signal corresponding to the oxidized or reduced indicator species after the step of electrochemically oxidizing or reducing the indicator species at least a second time. The concentration of the analyte is determined using the measured signals corresponding to the oxidized or reduced indicator species and the electrochemical oxidation or reduction charges. Although described in this paragraph generally as a change in oxidation or reduction, in practice the indicator species will either be reduced or oxidized, and not generally both.

In an embodiment, the analyte includes chlorine and the indicator species is chosen from N,N-Diethyl-p-phenylenediamine (DPD) and N,N-bis(2,4-di-sulfobenzyl)toluidinetetrasodium salt (SBT).

In an embodiment, the analyte includes nitrosamine and the indicator species is ferrate.

In an embodiment, at least some of the signals corresponding to the oxidized or reduced indicator species are optical signals.

In an embodiment, the steps of measuring the signals corresponding to the oxidized or reduced indicator species are performed using spectroscopy.

In an embodiment, the method further includes the steps of plotting a measured optical signal corresponding to the oxidized or reduced indicator species after chemical oxidation or reduction and after each step of electrochemically oxidizing or reducing the indicator species as a function of concentration of oxidized or reduced indicator species, generating thereby a curve; and determining the concentration of analyte from the curve.

In an embodiment, the steps of measuring the concentration of the oxidized or reduced indicator species are performed using either spectroscopy or electrochemistry.

In an embodiment, measuring a signal corresponding to the oxidized or reduced indicator species includes measuring an optical absorbance at a wavelength between 500 nm and 550 nm.

In an embodiment, the method is performed without the need for an additional calibration step.

Benefits and advantages of the present invention include, but are not limited to a method for determining the quantity of an analyte in a sample without the need for calibration curves, thereby eliminating matrix effects which become important for low analyte concentrations, since producing low-level, stable standards may be challenging.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
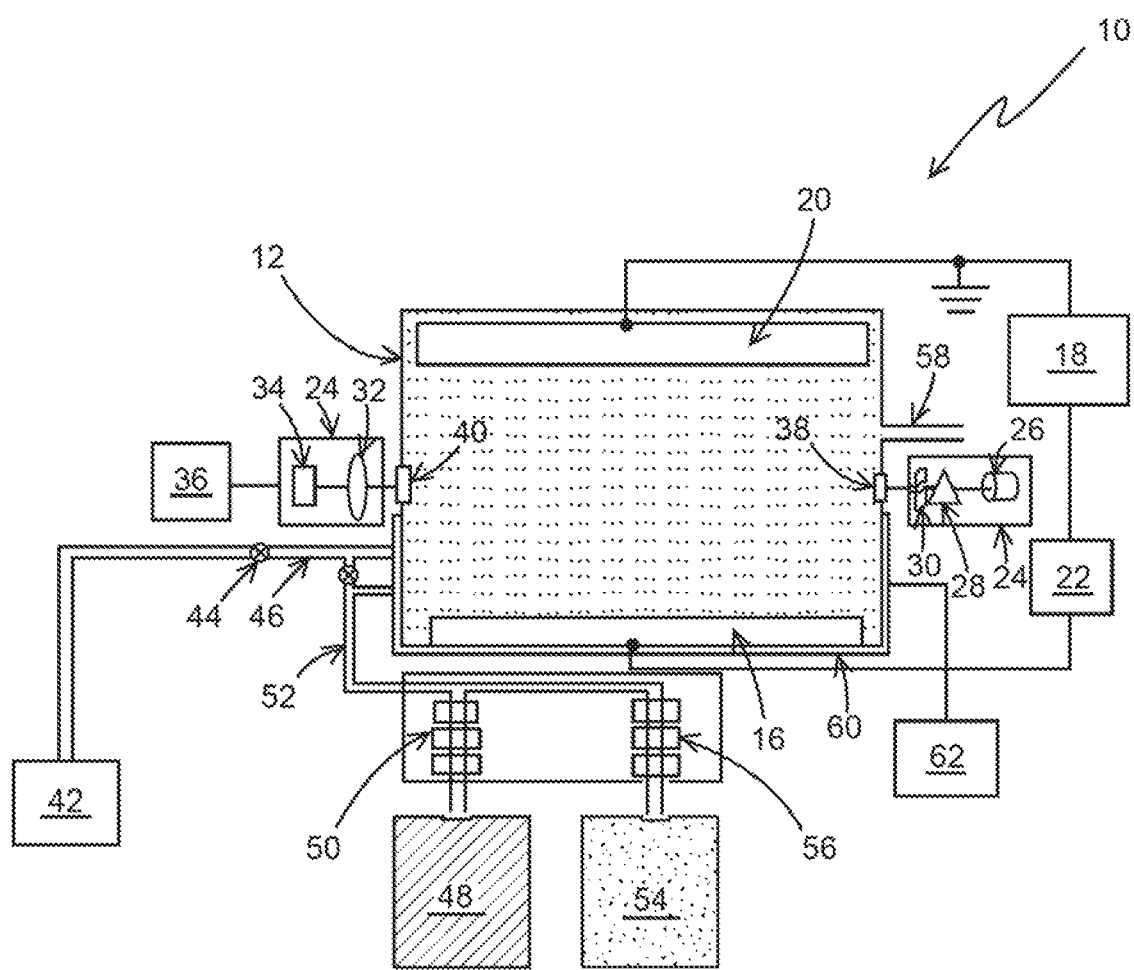
FIG. 1 is a schematic representation of an embodiment of a spectro-electrochemical system which may be used to determine ultra-low levels of chlorine.

The present disclosure provides a method of determining the concentration of an analyte using a combination of chemical and electrochemical redox reactions, without the need for a calibration step. Exemplary analytes that may be measured according the disclosed method include chlorine, nitrosamine, iron (VI), gases such as carbon dioxide, and pH. An advantage of the disclosed method is that there is no need for an additional calibration step.

In the disclosed method, to a solution of the analyte is added a molar excess of an indicator species which forms undergoes a redox reaction (e.g. is either oxidized or reduced) when contacted by the analyte. A signal (such as an optical signal) corresponding to the oxidized or reduced indicator species is measured. Then, the indicator species is electrochemically oxidized or reduced at a chosen voltage for a selected time period. The electrochemical oxidation or reduction charge is recorded, and a signal corresponding to the oxidized or reduction indicator species is measured. The step of electrochemically oxidizing or reducing the indicator species may be repeated multiple times. The concentration of the analyte is determined using the measured signals corresponding to the oxidized or reduced indicator species and the electrochemical oxidation or reduction charges. Preferably, the method is performed without the need for an additional calibration step.

Electrochemical quantitative generation of a detectable species provides specified quantities of the species, and permits the determination of an unknown analyte. Turning now to specific example, N,N-Diethyl-p-phenylenediamine (DPD), or N,N-bis(2,4-di-sulfobenzyl)toluidinetetrasodium salt (SBT), may be used for obtaining an in-situ calibration curve for free chlorine concentration measurements, thereby eliminating matrix effects. As another example, ferrate (Iron VI) may be used for obtaining an in-situ calibration curve for nitrosamine concentration measurements, thereby eliminating matrix effects The electrochemical activity (redox properties) of DPD may be used to determine the chlorine concentration (See, e.g., "Reaction with DPD: A procedure for Sensitive Square-Wave Voltammetric Detection of Chlorine," by E. H. Seymour et al., Electroanalysis, 2003, 15, No. 8 pp. 689-694.). DPD can be both chemically and electrochemically oxidized, the oxidized form of DPD being the quinone-imine form, according to the reactions:

First Half reaction: $HOCl+H^++2e^- \leftrightarrows Cl^-+H_2O$
Second Half reaction: $DPD\ (Ox)+2H^++2e^- \leftrightarrows DPD$
Sum reaction: $HOCl+DPD \leftrightarrows DPD\ (Ox)+H_2O+HCl$.

These reactions show that 1 mole of DPD is oxidized by 1 mole of HOCl, and that DPD(Ox) can be electrochemically added via electrochemical oxidation of DPD at a constant voltage, for example. The oxidation of DPD, provided in excess, by free chlorine reacts all of the chlorine present.

The amount of DPD that is electrochemically oxidized can be determined by monitoring the charge delivered to the system, according to the equation: $Q=nFV[DPD]$, where Q is the charge delivered to the system for oxidation of DPD, n is the number of electrons involved in the DPD oxidation process, F is Faraday's constant, V is the volume of the sample solution taken for analysis, and [DPD] is the concentration of DPD that is oxidized (See, e.g., *Electrochemical Methods: Fundamentals and Applications*, $2^{nd}$ edition, by A. J. Bard and L. R. Faulkner, Chapter: Bulk Electrolysis Methods, pp. 417-431.). Since one mole of DPD is oxidized for each mole of chlorine, the amount of chlorine in the unknown can be determined by measuring the DPD oxidized electrochemically. The DPD(Ox) produced by electrochemical oxidation of DPD can be determined by measuring the optical absorbance of the solution at a wavelength in the range of 510 nm to 530 nm, preferably about 515 nm, as an example. By plotting the amount of oxidized DPD and the optical data obtained from the DPD(Ox) and extrapolating the linear profile to the X-intercept, the concentration of the analyte of interest, such as chlorine, is determined. For other analytes and indicator species, such as nitrosamine and ferrate, a similar procedure may be used.

Reference will now be made in detail to the present embodiments of the invention, examples of which are illustrated in the accompanying drawings. In the FIGURES, similar structure will be identified using identical reference characters. It will be understood that the FIGURES are for describing particular embodiments of the invention and are not intended to limit the invention thereto. Turning now to FIG. 1, a schematic representation of an embodiment of spectro-electrochemical system, 10, which may be used to determine ultra-low levels of an analyte such as chlorine. Chamber, 12, contains solution, 14, comprising an indicator species such as DPD, chemically oxidized DPD, DPD electrochemically oxidized by anode, 16, powered by constant voltage current supply, 18, and grounded cathode, 20, and a buffer to maintain the pH at around neutral (pH of 6.9-7.1). Electrochemical oxidation current is measured using meter 22. Absorbance of the oxidized DPD in the solution is measured using standard optical instrumentation, 24, which may include light source, 26, optical dispersion element, 28, collimating slit, 30, collimating optics, 32, optical detector, 34, and control and recording electronics, 36, the light entering and leaving chamber 12 through transparent windows, 38 and 40, respectively.

Samples, 42, may be introduced directly into chamber 12 through valve, 44, and sample input tube, 46. DPD solution, 48, may be introduced into chamber 12 using peristaltic pump, 50, and input tubing, 52. Buffer solution, 54, may be introduced into chamber 12 using peristaltic pump, 56, and may include 10-50 mM of a 1-1 solution of potassium monohydrogen phosphate and potassium dihydrogen phosphate, which controls the pH to between about 6.9 and 7.1. Advantageously, 25 mM of solutions are employed. Fluid exits chamber 12 through exit tube, 58.

Chamber 12 may be kept at a chosen temperature using heating jacket, 60, shown as covering a portion of chamber 12, and controlled by temperature measurement and heat controller unit, 62. Jacket 60 can be utilized as covering the entire chamber 12.

Figure 2:
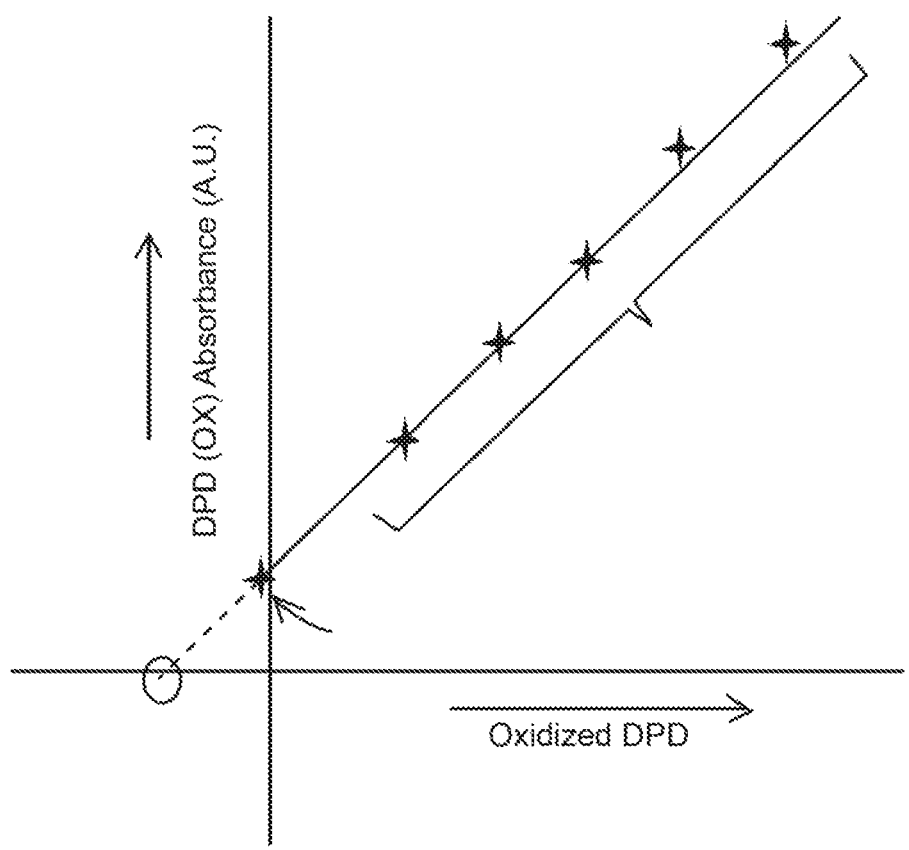
FIG. 2 is a graph of a signal generated by DPD(Ox) in solution, illustrated as an optical absorption signal in arbitrary units, as a function of the measured oxidation current, which is a measure of the electrochemical charge delivered to the system to generate the DPD(Ox).

Initially, a sample containing the free chlorine to be measured is introduced into the chamber where there is an excess of DPD. A portion of the DPD reacts with the chlorine, which oxidizes the DPD to DPD(Ox). After this reaction, there is no chlorine remaining in the chamber. If the quantity of chemically oxidized DPD is designated as "x", the concentration of DPD(Ox) due to chemical oxidation is "x". An electrochemical potential, V1, effective for oxidizing DPD is applied to the solution for time, t1, in seconds, to generate a quantity of DPD(Ox), "Dx1", yielding a total concentration of DPD(Ox) in the chamber of "x+Dx1". The current passed through the system for the period of t1 s can be used to determine "Dx1". After a chosen period where no voltage is applied, the system is subjected to a potential of V1 for t2 s, and the current is measured to produce additional DPD(Ox). That is, the color formation due to the electrochemical oxidation of DPD is continuously monitored after the application of the first voltage. Once a stable color reading is observed, it is recorded and the system is then ready for the next voltage step to generate more DPD(Ox). Again, the current passed may be used to determine the additional quantity of DPD(Ox)produced, or "Dx2", yielding a total DPD(Ox) in the chamber of "x+Dx1+Dx2". This process may be repeated a selected number of times, for example 5 oxidations in total, to obtain a DPD(Ox) concentration of "x+Dx1+Dx2+Dx3+Dx4+Dx5". Optical, electrochemical or both techniques may be used to generate signals which are proportional to the quantity of DPD(Ox) generated. The signals produced are then plotted (y-axis) against the electrochemical charge delivered for each step (x-axis), as illustrated in FIG. 2. The intercept indicated by the arrow at the y-axis will not be zero because of the DPD(Ox) produced by the chemical oxidation of DPD by the initial concentration of chlorine. The extrapolation of the linear curve to the x-axis yields the concentration of the DPD(Ox) produced by the oxidation of the free chlorine in the chamber. Thus, the electrochemical generation of the reagent permits the quantity of free chlorine in the chamber to be determined without calibration procedures using standard solutions, which is therefore independent of matrix effects in the sample. All of the calibration steps may be performed in minutes.

Electrochemical measurements may be made using a commercially available electrochemical potentiostat, which is used to apply the selected potential and measure the current for the chosen time duration. The delivered charge is then calculated manually or using a software program installed in the instrument.

If the linear curve is represented by y=mx+b, where m is the slope, and b is the intercept with the y-axis, the value of x which represents the DPD(Ox) produced by the chlorine is (−b/m). The present method can be used for any system which is capable of electrochemically generating the active or standard species. For example, an unknown pH may be determined by quantitatively electrochemically adding protons.

Having generally described the invention, the following EXAMPLES provide additional details.

EXAMPLE 1

The following steps may be performed using apparatus 10, as an example, for a typical chlorine determination:
1) N,N-Diethyl-p-phenylenediamine (DPD) was added to a sample solution with a quantity of chlorine.
2) After the DPD reacts with the chlorine a measurement of the chemically oxidized DPD was made by an optical absorption measurement at between 510-530 nm, and more specifically at 515 nm.
3) After the optical determination, additional DPD in the solution is electrochemical oxidized to DPD (Ox) at 0.5 V vs. Ag/AgCl at a Pt electrode for a chosen period of time, for example, 1 min. The charge delivered for this oxidation was recorded. The amount of DPD(Ox) was optically determined as the absorbance unit.
4) Step 3 was repeated a selected number of times, for example, 5 times and the charge and the optical measurement for each repetition is recorded. These repetitions generate the electrochemical standard addition.

The charge (Q) is determined by integrating current over time $Q(t)=\int i(t)\,dt$. This charge was used to determine the concentration of DPD that was oxidized for each step. The optical measurement of DPD(Ox) was also measured for each step. The table shows the measured charge, amount of DPD oxidized and the optical measurement of DPD(Ox). Household bleach, which is sodium hypochlorite, was used as the source of chlorine in the sample.

TABLE

| Type of oxidation | Charge (Q) Echem Meas. Milli Coulombs | Amount of DPD oxidized (C = Q/nFV); mol/L | DPD Ox absorbance Optical Meas. Absorbance (A.U) |
|---|---|---|---|
| Chemical by $Cl_2$ | 0 | 0.00E+00 | 0.383 |
| Electrochemical | 1.204 | 5.20E−07 | 0.419 |
| | 2.449 | 1.06E−06 | 0.448 |
| | 3.742 | 1.62E−06 | 0.473 |
| | 5.606 | 2.42E−06 | 0.499 |
| | 7.357 | 3.18E−06 | 0.52 |
| | 10.717 | 4.63E−06 | 0.565 |

Figure 3:
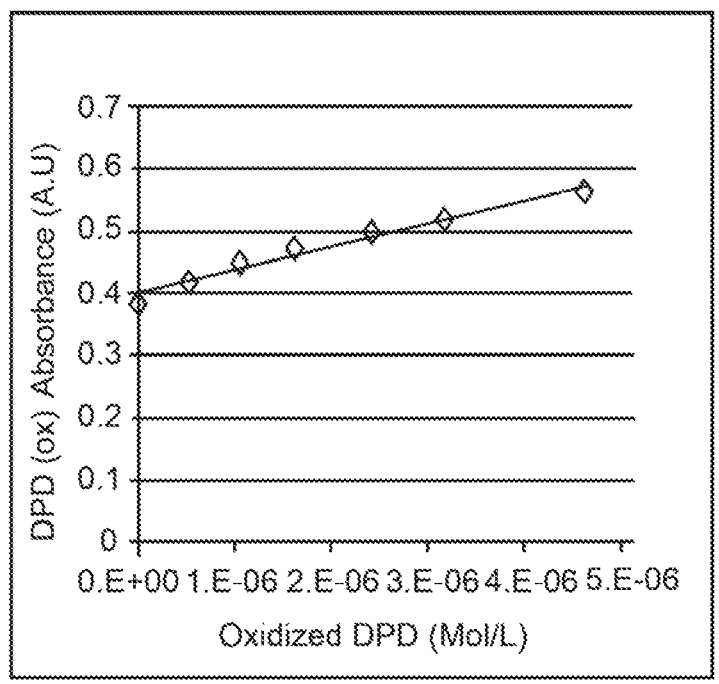
FIG. 3 is a graph of the electrochemical standard addition/calibration measured using DPD, illustrating a slight deviation from linearity.
Figure 4:
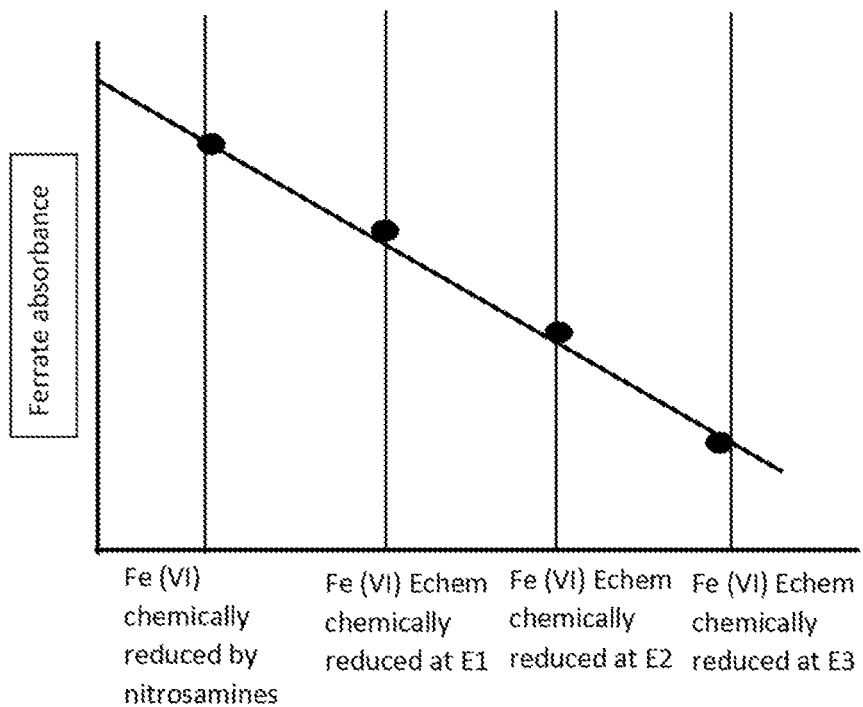
FIG. 4 is a graph of the ferrate absorbance of a sample illustrated in Example 2.

FIG. 3 is a graph of data in the Table, showing the electrochemical standard addition/calibration using DPD and household bleach, as a chlorine source. The graph in FIG. 3 shows a slight deviation from linearity. This deviation might be due to the electrochemical oxidation efficiency. Correction such efficiencies may improve the linearity of the plot. The x-intercept is obtained by setting y=0. See, e.g., Quantitative Chemical Analysis, 5$^{th}$ edition, D. C. Harris, pp 101-107. As previously described, the x-intercept (y=0) provides the concentration of DPD that is oxidized by chlorine, since 1 mole chlorine, oxidizes 1 mole of DPD according to the stoichiometric equation previously provided. Hence, the unknown chlorine concentration was determined to be 0.74 mg/L in this system. This concentration was compared with the standard chlorine determination method and was found to be 0.62 mg/L. This observed 20% difference between the two methods which may be due to: (1) the volume of the sample solution was not controlled accurately; (2) a correction factor for the efficiency of the electrochemical bulk oxidation of the DPD must be applied; and (3) DPD chemical method can be influenced by matrix effects.

EXAMPLE 2

The following steps may be performed using apparatus 10, as an example for determining the concentration of nitrosoamines using ferrate as an indicator species.

Step 1. Ferrate (Iron (VI)) is added to the sample solution with an unknown quantity of nitrosamines (for example, N-Nitrosodimethylamine).

Step 2. After the ferrate reacts with Nitrosoamines, a measurement of the ferrate is made by an optical absorption measurement between 500-550 nm, and more specifically at 505 nm. This absorption of ferrate (Fe (VI)) would decrease (Dx) from its initial value (X) to the chemical oxidation of nitrosamines (X-Dx).

Step 3. After the optical determination, additional ferrate (Fe (VI)) in the solution is electrochemically reduced to Fe (V) or Fe (IV) or Fe (III) or Fe (II) at the appropriate reduction potentials (−0.5, −0.6, −0.7 or −0.8) vs. Ag/Ag Cl at an inert electrode like Pt, Au or solid boron doped diamond for chosen period of time, for example 1-5 minutes. The charge delivered for this reduction is recorded. The amount of Fe (VI) consumed is measured by a decrease in absorbance, because Fe (V) and lower valent species do not absorb at the same wavelength as Fe (VI) at 505 nm Step 4. Step 3 may be repeated a selected number of times, for example, 5 times and the charge and optical measurement for each repetition is recorded. These repetitions generate the electrochemical standard curve.

EXAMPLE 3

Low concentrations of aqueous Fe(VI) can be determined by the reaction of Fe (VI) with 2,2'-azino-bis(3-ethylbenzothiazoline-6-sulfonate) (ABTS) using the electrochemical standard addition method by generating an in-situ echem standard addition method. Fe(VI) reacts with 2,2'-azino-bis (3-ethylbenzothiazoline-6-sulfonate) which forms a green colored oxidized (ABTS (Ox)) that can be measured spectrophotometrically at 415 nm. The ABTS can be electrochemically oxidized to green color as per the following reactions:

ABTS−·+e−→ABTS2−E°'=0.67 V vs SHE
ABTS+e−→ABTS−·E°'=1.08 V vs SHE

Thus, after the initial chemical oxidation of ABTS by Fe(VI) the later oxidation of ABTS can be carried out by electrochemical means to generate the standard curve which then can be used to determine low concentrations (typically 0-100 um) ferrate. This can be applied to other oxidant species like oxygen, hydrogen peroxide, higher valent transition metal species like Cr(VI), Mn (VII).

EXAMPLE 4

Gaseous species like carbon dioxide can be determined by this method. The Hach Company "Test in tube" method for determining total organic carbon (as described in patent EP1605260B1) uses a thymol blue indicator to quantify the $CO_2$. The $CO_2$ is produced by UV oxidation of the organic compound. The initial $CO_2$ present will affect the pH and this in turn will chemically react with thymol blue to produce a color. Subsequently the organic carbon can be oxidized electrochemically to $CO_2$ which then affects the pH. This change in pH will also react with thymol blue which will affect the color. This changes in color can be used to quantify the $CO_2$ that is initially present in the sample.

EXAMPLE 5

The pH of a solution can be determined by this method without the need for a calibration step. The initial pH will react with thymol blue or any other pH indicator like methyl red or bromocresol green. Later the protons or hydroxides can be generated electrochemically (oxidation or reduction or water) to increase or decrease the pH which affects the color. This in-situ increase or decrease in color can be used to quantify the pH of the solution without the need to calibrate the system.

It will be apparent that the general techniques described above for the measurement of chlorine, nitrosamine, iron (VI), carbon dioxide, and pH may be applied to many other analytes, using an appropriate indicator species. As described, the indicator species may be either oxidized or reduced during the measurement process.

The foregoing description of the invention has been presented for purposes of illustration and description and is not intended to be exhaustive or to limit the invention to the precise form disclosed, and of course many modifications and variations are possible in light of the above teaching. The embodiments were chosen and described to best explain the principles of the invention and its practical application to thereby enable others skilled in the art to best utilize the invention in various embodiments and with various modifications as are suited to the particular use contemplated. It is intended that the scope of the invention be defined by the claims appended hereto.

The invention claimed is:

1. A method for determination of the concentration of an analyte in a solution, comprising:
providing a sample of the solution comprising the analyte, wherein the analyte is selected from the group consisting of: chlorine, iron (VI), and carbon dioxide;
adding to the solution a molar excess of an electrochemically and chemically oxidizable indicator species which forms an oxidized species when contacted by the analyte, wherein the oxidizable indicator species is selected from the group consisting of: N, N-Diethyl-p-phenylenediamine (DPD), N,N-bis(2,4-di-sulfobenzyl) toluidinetetrasodium salt (SBT), and 2,2'-azino-bis(3-ethylbenzothiazoline-6-sulfonate) (ABTS);
allowing the indicator species to be chemically oxidized by the analyte to provide an oxidized indicator species;
measuring, using spectroscopy, a signal corresponding to the oxidized indicator species after chemical oxidization thereof by the analyte;
electrochemically oxidizing the indicator species at a chosen voltage for a selected time period, whereby a first electrochemical oxidation charge is passed;
recording the first electrochemical oxidation charge;
measuring, using spectroscopy, a signal corresponding to the oxidized indicator species after the step of electrochemically oxidizing the indicator species;
repeating the step of electrochemically oxidizing the indicator species at least a second time, whereby at least one second oxidation charge is passed;
recording the at least one second electrochemical oxidation charge; and
measuring, using spectroscopy, a signal corresponding to the oxidized indicator species after the step of electrochemically oxidizing the indicator species at least a second time,
whereby the concentration of the analyte is determined using the measured signals corresponding to the oxidized indicator species and the electrochemical oxidation charges.

2. The method of claim 1, wherein at least some of the signals corresponding to the oxidized indicator species are optical signals.

3. The method of claim 1, further comprising the steps of plotting a measured optical signal corresponding to the oxidized indicator species after chemical oxidation and after each step of electrochemically oxidizing the indicator species as a function of concentration of oxidized indicator species, generating thereby a curve; and
determining the concentration of analyte from the curve.

4. The method of claim 1, wherein the analyte comprises chlorine, and the indicator species is chosen from N,N-Diethyl-p-phenylenediamine ("DPD"), and N,N-bis (2,4-di-sulfobenzyl) toluidine tetrasodium salt ("SBT").

5. The method of claim 1, wherein measuring a signal corresponding to the oxidized indicator species comprises measuring an optical absorbance at a wavelength between 500 nm and 550 nm.

6. The method of claim 5, wherein measuring a signal corresponding to the oxidized indicator species comprises measuring an optical absorbance at a wavelength of about 515 nm.

\* \* \* \* \*